United States Patent
Barker et al.

(10) Patent No.: US 10,258,980 B2
(45) Date of Patent: Apr. 16, 2019

(54) PURE CHELATION PROCESS

(71) Applicants: C LAB PHARMA INTERNATIONAL, S.A., Tortola (VG); Charles Louis Albartus Barker, Flagstaff, AZ (US); Siead Zegar, Orland Park, IL (US); Kurt L. Wachholder, Gilberts, IL (US)

(72) Inventors: Charles Louis Albartus Barker, Flagstaff, AZ (US); Siead Zegar, Orland Park, IL (US); Kurt Wachholder, Gilberts, IL (US)

(73) Assignee: C Lab Pharma International, S.A., Torola (VG)

( * ) Notice: Subject to any disclaimer, the term of this patent is extended or adjusted under 35 U.S.C. 154(b) by 15 days.

(21) Appl. No.: 15/509,142

(22) PCT Filed: Sep. 8, 2015

(86) PCT No.: PCT/US2015/048914
§ 371 (c)(1),
(2) Date: Mar. 6, 2017

(87) PCT Pub. No.: WO2016/037181
PCT Pub. Date: Mar. 10, 2016

(65) Prior Publication Data
US 2017/0274370 A1    Sep. 28, 2017

Related U.S. Application Data

(60) Provisional application No. 62/046,947, filed on Sep. 6, 2014.

(51) Int. Cl.
*B01J 45/00* (2006.01)
*A61K 31/28* (2006.01)
*A61K 31/30* (2006.01)
*A61K 31/315* (2006.01)
*C07F 13/00* (2006.01)

(52) U.S. Cl.
CPC .............. *B01J 45/00* (2013.01); *A61K 31/28* (2013.01); *A61K 31/30* (2013.01); *A61K 31/315* (2013.01); *C07F 13/005* (2013.01)

(58) Field of Classification Search
CPC ....................................................... B01J 45/00
USPC ............................................................ 546/2
See application file for complete search history.

(56) References Cited

U.S. PATENT DOCUMENTS

| | | | |
|---|---|---|---|
| 4,183,947 A | 1/1980 | Cockerill | |
| 4,612,175 A | 9/1986 | Harkness et al. | |
| 5,292,729 A * | 3/1994 | Ashmead | A61K 31/44 514/168 |
| 5,504,055 A | 4/1996 | Hsu | |
| 2011/0274773 A1* | 11/2011 | Hussein Aly Ibraheim | A61K 31/455 424/728 |

FOREIGN PATENT DOCUMENTS

CN    1931844 A    3/2007

OTHER PUBLICATIONS

Goher, Inorganica Chinnica Acata, 1987, 127, I13-16.*
Goher, Collection Czechoslov. Chem. Commun. [vol. 40] (1975), 26-35Chinese.*

* cited by examiner

*Primary Examiner* — Nizal S Chandrakumar
(74) *Attorney, Agent, or Firm* — Rodney J. Fuller; Booth Udall Fuller, PLC

(57) ABSTRACT

The present invention relates to metal complexes and methods of synthesizing the metal complexes. The invention is further directed to pharmaceutical and/or dietary supplement composition comprising compounds synthesized as described herein.

11 Claims, 6 Drawing Sheets

A.

B.

| Element Line | Weight % | Weight % Error |
|---|---|---|
| C K | 53.70 | ± 0.17 |
| N K | 12.08 | ± 0.45 |
| O K | 19.52 | ± 0.15 |
| Cl K | 4.87 | ± 0.04 |
| Cu K | 9.82 | ± 0.23 |
| Pd L | 0.00 | --- |
| Total | 100.00 | |

A.

B.

| Element Line | Weight % | Weight % Error |
|---|---|---|
| C K | 50.88 | ± 0.15 |
| N K | 17.80 | ± 0.46 |
| O K | 29.10 | ± 0.18 |
| Al K | 0.23 | ± 0.02 |
| Cl K | 1.98 | ± 0.03 |
| Pd L | 0.00 | --- |
| Total | 100.00 | |

A.

B.

| Element Line | Weight % | Weight % Error |
|---|---|---|
| C K | 42.65 | ± 0.17 |
| N K | 8.11 | ± 0.31 |
| O K | 14.24 | ± 0.12 |
| Cl K | 12.10 | ± 0.06 |
| Cu K | 22.90 | ± 0.26 |
| Pd L | 0.00 | --- |
| Total | 100.00 | |

A.

B.

| Element Line | Weight % | Weight % Error |
|---|---|---|
| C K | 40.33 | ± 0.16 |
| N K | 9.19 | ± 0.28 |
| O K | 16.16 | ± 0.11 |
| Al K | 0.49 | ± 0.02 |
| Si K | 0.04 | ± 0.01 |
| Cl K | 12.51 | ± 0.05 |
| Cu K | 21.27 | ± 0.23 |
| Pd L | 0.00 | --- |
| Total | 100.00 | |

PURE CHELATION PROCESS

CROSS REFERENCE TO RELATED APPLICATIONS

This application is the U.S. National Stage of International Application No. PCT/US2015/048914, filed on Sep. 8, 2015, which claims priority to and the benefit of U.S. Provisional Patent Application No. 62/046,947filed on Sep. 6, 2014, the contents of each of which are incorporated herein by reference in their entireties.

BACKGROUND OF THE INVENTION

Certain metals, such as cobalt, copper, iron, manganese, and zinc, play an essential role for optimal health. Cobalt is the key constituent of vitamin $B_{12}$, which is a cofactor for methylmalony-CoA mutase and methionine synthase in humans. (Sigel et al., *Met. Ions Life Sci.* 13 (2013) 295-320). Copper is essential in any organism that have an oxidative metabolism. (Scheiber et al., *Met. Ions Life Sci.* 13 (2013) 359-387). Copper is a component of multiple enzymes involved in reducing molecular oxygen; of multiple enzymes involved in metabolizing substances such as histamine, serotonin, epinephrine, and dopamine; of multiple enzymes that oxidize ferrous iron and facilitate binding of iron to transferrin; and of cytochrome c oxidase, which is a critical player in energy production. (Council for Responsible Nutrition. Recommended Intakes of Vitamins and Essential Minerals; 2002). While iron is also a component of multiple enzymes, for example cytochromes, iron-sulfur enzymes, and other enzymes, iron is also an important part of hemoglobin and myoglobin, which play the important role of oxygen diffusion facilitators in tissues. (Institute of Medicine (US) Panel on Micronutrients. Dietary Reference Intakes for Vitamin A, Vitamin K, Arsenic, Boron, Chromium, Copper, Iodine, Iron, Manganese, Molybdenum, Nickel, Silicon, Vanadium, and Zinc. Washington (DC): National Academies Press (US); 2001. 9, Iron). As with the other metals, manganese and zinc are components of various enzymes. Manganese is involved in enzymes playing roles in the formation of bone and in the metabolism of amino acids, lipids, and carbohydrates. (Council for Responsible Nutrition. Recommended Intakes of Vitamins and Essential Minerals; 2002). Zinc functions as a component of numerous enzymes in the maintenance of the structural integrity of proteins and in the regulation of gene expression. (Institute of Medicine (US) Panel on Micronutrients. Dietary Reference Intakes for Vitamin A, Vitamin K, Arsenic, Boron, Chromium, Copper, Iodine, Iron, Manganese, Molybdenum, Nickel, Silicon, Vanadium, and Zinc. Washington (DC): National Academies Press (US); 2001. 12, Zinc).

Other minerals, such as nickel, have not been given essential mineral status, but their role in structure components or cofactors for enzymes suggest they also play important roles for optimal health. Nickel is a cofactor or structural component of metalloenzymes involved in hydrolysis, redox reactions, and gene expression, among other functions. (Institute of Medicine (US) Panel on Micronutrients. Dietary Reference Intakes for Vitamin A, Vitamin K, Arsenic, Boron, Chromium, Copper, Iodine, Iron, Manganese, Molybdenum, Nickel, Silicon, Vanadium, and Zinc. Washington (DC): National Academies Press (US); 2001. 13, Arsenic, Boron, Nickel, Silicon, and Vanadium).

While the best way to get minerals into the body needs is by eating a variety of foods, sometimes a mineral supplement is needed. Since the use of chelated minerals, where a metal ion is bound to a chelating agent, to supplement minerals in animal feed, mineral supplements for human consumption also started using chelated metals as dietary supplements. However, the cost of chelating minerals has provided the widespread use of chelated minerals in spite of experimental data showing that chelated metals have bioavailability. Thus there is a need for lower cost methods for synthesizing chelated minerals.

SUMMARY OF THE INVENTION

The present invention is directed to a method of synthesizing chelated metals. The present invention further includes compounds synthesized according to the claimed method and uses thereof. In one specific embodiment, the invention is directed to a method comprising ionizing a metal salt in water to produce an aqueous solution of metal ions; solubilizing a chelating agent in water to produce an aqueous solution of chelating agent; mixing the aqueous solution of metal ions with the aqueous solution of chelating agent to produce an aqueous solution of metal chelate; precipitating the aqueous solution of metal chelate by adjusting the pH to between about 3 and about 4 to produce a precipitated aqueous solution of metal chelate. The method is typically conducted in an oxygen-free environment.

In certain non-limiting embodiments, the methods of the invention further comprise cooling the precipitated aqueous solution of metal chelate; collecting the precipitate from the precipitated aqueous solution of metal chelate; and washing the precipitate with ascorbic acid followed by absolute alcohol. In certain specific embodiments, the step of ionizing a metal in water and/or the step of solubilizing a chelating agent in water are/is performed in a first nitrogen-purged reactor.

The metal ionized by the methods of the invention may be a transition metal, or preferably a group 7 transition metal, for example, copper, cobalt, nickel, zinc, or manganese. In some embodiments, the metal may be ionized in a mixture of water and hydrochloric acid. For certain embodiments, the chelating agent is an organic compound, for example, nicotinic acid, an amino acid, and/or a mixture of amino acids.

DETAILED DESCRIPTION OF THE INVENTION

Figure 1:
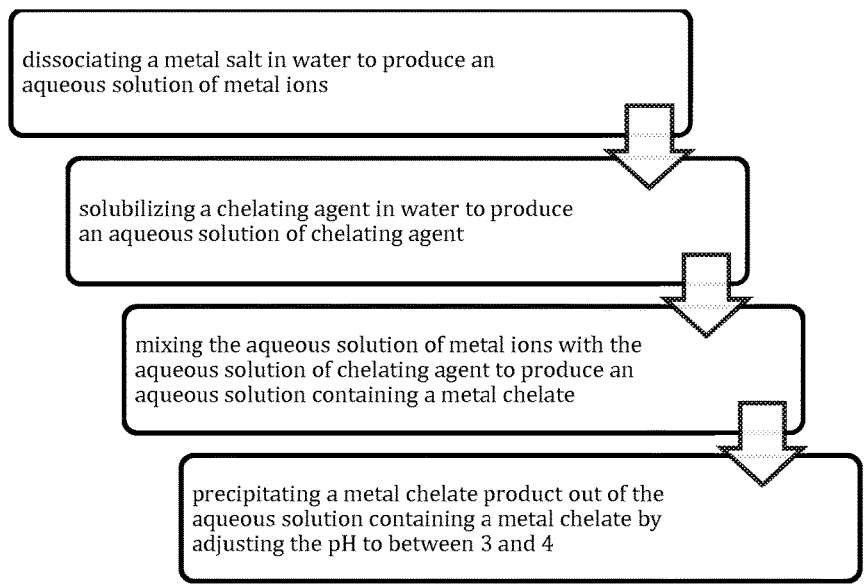
FIGS. 1 and 2 depict flow charts of two specific non-limiting examples of the pure chelation process.
Figure 2:
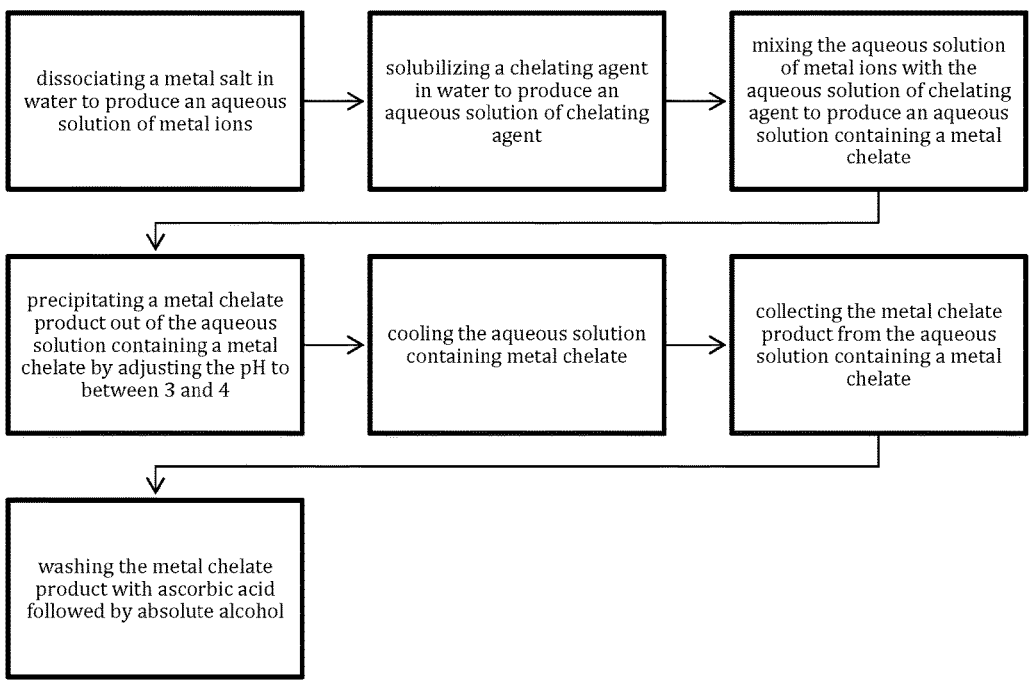

The verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

The term "metal" as used herein refers to a substance with high electrical conductivity, which readily loses electrons to form positive ions, for example transition metals. For example, metals may refer to cobalt, copper, manganese, nickel, and zinc. Metals may also refer to group 7 transition metals.

The term "chelating agent" as used herein refers to a substance whose molecules can form at least two separate dipolar bonds to a single metal. Thus a chelating agent is a multidentate ligand. Examples a chelating agent include organic molecules, such as nicotinic acid and succinic acid, polypeptides, and amino acids, such as glycine and methionine. Chelating agents may be naturally occurring or synthetic.

The terms "chelated metal" and "metal chelate" as used herein are interchangeable and refer to a metal that is bound to a chelating agent. Thus chelated copper and copper chelate both refer to copper that is bound to a chelating agent.

The term "room temperature" as used herein refers to a temperature falling between of between 20° C. and 26° C. For example, room temperature can be 20° C., 21° C., 22° C., 23° C., 24° C., 25° C., or 26° C. Room temperature can also refer to a range between 20° C. to 23° C. or 20° C. to 22° C.

The terms "copper (I) complex" and "copper (I) compound" as used herein are interchangeable and refer to a chemical compound in which copper is present in its +1 oxidation state and interacts with at least one compound through ionic or covalent bonding. Thus chelated copper would be a copper (I) complex or a copper (I) compound.

Pure Chelation Process

The present invention relates to methods of chelating minerals for dietary supplements that has improved yield, improved purity. In preferred embodiments, the oxidative states of the chelated minerals produced by the methods of invention match the oxidative state of the mineral found in nature. For example, in copper in plants is found in the +1 oxidative state.

The methods can be scaled up for production of metric tons of the chelated metal or scaled down for bench-top amounts of chelation chemistry to make merely grams of the chelated metal. The pure chelation process comprises dissociating a metal, such as a salt in water to produce an aqueous solution of metal ions and solubilizing a chelating agent in water to produce an aqueous solution of chelating agent. The method further comprises mixing the aqueous solution of metal ions with the aqueous solution of chelating agent to produce an aqueous solution containing a metal chelate; and precipitating a metal chelate product out of the aqueous solution containing a metal chelate by adjusting the pH to between 3 and 4.

In one embodiment, the metal is ionized in water solution comprising hydrochloric acid. The amount of hydrochloric acid may be between 1 g to 10 g per gram of metal, between 2.5 g to 10 g per gram of metal, between 2.5 g to 7.5 g per gram of metal, between 2.5 g to 5 g per gram of metal, between 3 g to 5 g per gram of metal, or about 5 g per gram of metal. Embodiments of the invention may also require that the metal be fully dissolved in the aqueous solution, whether comprising solely of water or of water and hydrochloric acid. For example, some embodiments of the invention may require that the metal be stirred with the aqueous solution for at least 15 minutes at room temperature. The temperature at which the aqueous solution of metal ions is stirred and the duration of stirring may vary depending on the type of metal used. Generally, the higher the temperature, the less the duration of stirring.

In another embodiment, the chelating agent is solubilized in a solution with water and ascorbic acid. To ensure that the chelating agent is completely solubilized, the mixture comprising the chelating agent and water and in some embodiments ascorbic acid is heated. For example, the mixture is heated to a temperature of at least 70° C., at least 75° C., at least 80° C., at least 85° C., at least 90° C., or at least 95° C. The mixture may also be heated 70° C. to a temperature of between 70° C. to 75° C., 75° C. to 80° C., 80° C. to 85° C., 85° C. to 90° C., or 90° C. to 95° C. Stirring during this step would help solubilize the chelating agent in the water-based solvent. For example, in some embodiments, the solution is stirred at 70° C. to 75° C. for one to two hours until the chelating agent is completely solubilized.

While mixing aqueous solution of metal ions with the aqueous solution of chelating agent, some embodiments require that the aqueous solution of metal ions be slowly mixed into the aqueous solution of chelating agent. For example, the aqueous solution of metal ions is slowly mixed into the aqueous solution of chelating agent over the span of 45 minutes, 60 minutes, 75 minutes, 90 minutes, 120 minutes, or longer depending on the volume of aqueous solution of metal ions. In some embodiments, while the two aqueous solutions are being mixed, the solution comprising metal chelate is maintained between at a high enough temperature to ensure that the solution is entirely aqueous. For example, the aqueous solution containing a metal chelate is maintained at a temperature of at least 70° C., at least 75° C., at least 80° C., at least 85° C., at least 90° C., or at least 95° C. The aqueous solution containing a metal chelate may also be heated to a temperature of between 70° C. to 75° C., 75° C. to 80° C., 80° C. to 85° C., 85° C. to 90° C., or 90° C. to 95° C.

For precipitating a metal chelate out of the aqueous solution containing metal chelate by adjusting the pH, some embodiments requiring cooling the aqueous solution of metal chelate to less than 25° C. In preferred embodiments, the cooling process is gradual, for example, over the period of at least 12 hours, such as overnight. Some embodiments of the method adjust the pH with the addition of a base, such as sodium hydroxide. Other bases, such as strong bases like lithium hydroxide, potassium hydroxide, rubidium hydroxide, and cesium hydroxide, may also be used. While adjusting the pH, the temperature of the aqueous solution of metal chelate should be less than 35° C. In a preferred embodiment, the final pH of the aqueous solution of metal chelate should be between pH 3 to pH 3.8, pH 3.2 to pH 3.8, pH 3.4 to pH 3.8, pH 3.6 to pH 3.8, pH 3 to pH 3.6, pH 3.2 to pH 3.6, pH 3.4 to pH 3.6, pH 3 to pH 3.4, or pH 3.2 to pH 3.4.

Prior to collecting the metal chelate product from the aqueous solution containing a metal chelate, the temperature of the precipitated aqueous solution containing a metal chelate must be less than 25° C., less than 20° C., or less than 15° C. For some embodiments, the temperature of the precipitated aqueous solution containing a metal chelate is between 15° C. to 25° C., or more preferably between 15° C. to 20° C. The temperature may be cooled through stirring the precipitated aqueous solution containing a metal chelate for at least one hour. Because temperature can affect the pH of the solution, the pH of the cooled precipitated aqueous solution containing a metal chelate should be checked that it falls within pH 3 to pH 4, pH 3 to pH 3.8, pH 3.2 to pH 3.8, pH 3.4 to pH 3.8, pH 3.6 to pH 3.8, pH 3 to pH 3.6, pH 3.2 to pH 3.6, pH 3.4 to pH 3.6, pH 3 to pH 3.4, or pH 3.2 to pH 3. The methods for collecting the metal chelate product from the precipitated aqueous solution containing a metal chelate are known in the art. For example, the aqueous portion of the precipitated aqueous solution containing a metal chelate may be drained to isolate the metal chelate product. This may be centrifuging the precipitated aqueous solution containing a metal chelate. After the metal chelate product is isolated, the metal chelate product should be washed first with ascorbic acid followed by absolute alcohol. The washing step may also be performed with a centrifuge or any conventional method known to one having skill in the art.

In some embodiments, the method further comprises drying the metal chelate product in a vacuum. For example, the metal chelate product may be dried in a vacuum filled with an inert gas, such as nitrogen, overnight. The temperature of the vacuum may be between 40° C. to 80° C., 40° C. to 75° C., 40° C. to 70° C., 40° C. to 65° C., 45° C. to 80° C., 45° C. to 75° C., 45° C. to 70° C., 45° C. to 65° C., 50° C. to 80° C., 50° C. to 75° C., 50° C. to 70° C., 50° C. to 65° C., 55° C. to 80° C., 55° C. to 75° C., 55° C. to 70° C., 55° C. to 65° C., 60° C. to 80° C., 60° C. to 75° C., 60° C. to 70° C., 60° C. to 65° C., 65° C. to 80° C., 65° C. to 75° C., 65° C. to 70° C., 70° C. to 80° C., 70° C. to 75° C., or 75° C. to 80° C.

The entirety of the pure chelation process is conducted in an oxygen-free environment. For example, the metal salt is dissociated in a nitrogen-purged reactor, while the chelating agent is ionized in another nitrogen-purged reactor. During the reactions, both reactors are continuously purged with nitrogen gas. Other inert gases may be used to purge the reactors instead of nitrogen. Collecting the metal chelate product from the precipitated aqueous solution containing a metal chelate and drying the metal chelate product may also take place in an environment filled with inert gas, for example a centrifuge or vacuum purged with inert gas. The absence of oxygen gas in the reaction is critical, because reactions take place in a water-based solvent. The presence would oxygen would result in the oxidation of the metals, which reduces the value of the metal chelates as dietary supplements.

The starting amounts of metal, chelating agent, water, and for some embodiments, hydrochloric acid and ascorbic acid will vary depending on the metal and the chelating agent. However, the limiting reagent in the pure chelation process is the metal. Thus at least the chelating agent is in molar excess of the metal.

Example: Making Copper Nicotinic Acid

Copper plays a role in transporting oxygen throughout the body. It is an essential element for several enzymes systems essential for optimal metabolic function, including the electron transport chain, superoxide dismutase, and metalloproteases. (Beem J BIOL CHEM 249:7298 (1974)). Thus copper is important for the regulations of redox metabolism and the proper function of the mitochondria. Both abnormal regulation of redox metabolism resulting in oxidative stress and dysfunction of the mitochondria are associated with diseases, physical ailments, and disorders. The production of collagen, which determines the integrity of bones, skin, cartilage, and tendons, is copper-dependent. Copper is also crucial for making melanin, which provides color to skin and hair. Copper helps keep blood vessels elastic, is needed for the formation of elastin, functions as an iron oxidizer, and is needed for the proper functioning of vitamin C. For these and many other reasons, copper is required for optimal human health.

The two principal oxidation states of copper are +1 and +2, although some +3 complexes are known. Copper (I) compounds, often called cuprous compounds, are expected to be diamagnetic in nature and are usually colorless, except where color results from charge transfer or from the anion. The +1 ion has tetrahedral or square planar geometry. In solid compounds, copper (I) is often the more stable oxidation state at moderate temperatures. The copper (II) ion is usually the more stable state in aqueous solutions. Compounds of this ion, often called cupric compounds, are usually colored. They are affected by Jahn Teller distortions and exhibit a wide range of stereochemistries with four, five, and six coordination compounds predominating. The +2 ion often shows distorted tetrahedral geometry.

Complexes of copper (I) are thought to have a unique mechanism of action in promoting aerobic respiration via the electron transport chain. By causing the mitochondria in the cells to produce adenosine triphosphate (ATP) more efficiently and avoiding the production of lactic acid and ethanol that accompanies anaerobic respiration, pharmaceutical preparations and dietary supplements with copper (I) may alleviate and treat many illness and diseases. Among these diseases are those involving neuromuscular degeneration, muscle weakness, and autism spectrum disorders. Accordingly, there is a need to develop novel copper (I) compounds that may stimulate ATP production in the mitochondria.

Steps for Making Copper Nicotinic Acid (Copper Nicotinate) Using the Conventional Method A 72-liter three-neck round-bottomed flask equipped with a mechanical stirrer, reflux condenser, and a solid addition funnel is used to mix the chelating agent, nicotinic acid, with the metal, copper in the form of copper (I) chloride. The flask is maintained under slight positive pressure of nitrogen and is supported on a heating mantle.

1. Charge the flask charged with nicotinic acid (1.5 kg, 12.18 mol), ascorbic acid (0.65 kg, 3.86 mol), and 90% aqueous ethanol (20.4 L).
2. Stir the resulting white suspension and gently heat to 45° C.
3. Over the course of 15 minutes, gradually add copper (I) chloride (408.2 g, 4.12 mol) portion-wise into the flask through the solid addition funnel.
4. Place the copper/nicotinic acid/ascorbic acid mixture under flux and stir continuously overnight, which is about 19 hours.
5. Upon cooling copper/nicotinic acid/ascorbic acid mixture to 45° C., filter mixture under suction.
6. Wash the red precipitate sequentially first with ascorbic acid solution, 5% w/v (17 L), followed by ethanol (6.8 L), and finally with acetone (4 L).

7. Collect and dry red precipitate at 30° C.

Steps for Making Copper Nicotinic Acid Using the Pure Chelation Process

Nitrogen-purged glass-lined Pfaudler reactors are used to create the chelating agent mixture, which comprises water, ascorbic acid, and nicotinic acid, and to create the ionized metal, which comprises copper (I) chloride in water. The reactors are kept under nitrogen through the entire process.

1. Charge a first nitrogen-purged glass-lined Pfaudler reactor with water (809.60 kg). For every kilogram of copper (I) chloride used in the pure chelation process, use 36.8 kg water.
2. Stir while charging with nicotinic acid (80.96 g) and ascorbic acid (36.74 g). A precipitate will be formed. For every kilogram of copper (I) chloride used in the pure chelation process, use 3.28 kg nicotinic acid and 1.67 kg ascorbic acid.
3. Heat the resulting nicotinic acid/ascorbic acid mixture to between 70° C. to 75° C. to completely dissolve the precipitate.
4. Charge a second nitrogen-purged reactor with water (175.78 kg). For every kilogram of copper (I) chloride used in the pure chelation process, use 7.99 kg water.
5. Stir and charge this second reactor with hydrochloric acid (105.60 kg). Maintain stirring. For every kilogram of copper (I) chloride used in the pure chelation process, use 4.80 kg hydrochloric acid.
6. Charge copper (I) chloride (22.0 kg) to stirring hydrochloric acid solution and stir the copper mixture for 15 minutes at room temperature. Copper (I) chloride should be completely dissolved by then. If it is not, keep stirring until all of the copper (I) chloride has dissolved.
7. Gradually charge copper mixture to nicotinic acid/ascorbic acid mixture while maintaining the temperature between 70° C. to 75° C. It should take approximately 45 minutes to completed add the copper mixture into the nicotinic acid/ascorbic acid mixture.
8. Stir copper/nicotinic acid/ascorbic acid mixture for one to two hours while maintaining the temperature of the mixture at between 70 ° C. to 75° C. The solution should be a yellowish in color.
9. Cool the copper/nicotinic acid/ascorbic acid mixture to less than 25° C. This will take overnight, which is around 19 hours.
10. Adjust the pH of copper/nicotinic acid/ascorbic acid mixture to pH 3.4-pH 3.6 with addition of 50% aq NaOH (92.50 kg) while maintaining temperature below 35° C. For every kilogram of copper (I) chloride used in the pure chelation process, approximately 4 kg sodium hydroxide is needed to adjust the pH of copper/nicotinic acid/ascorbic acid mixture to pH 3.4-pH 3.6.
11. Cool resulting suspension to between 15° C. to 25° C.
12. Stir for at least one hour. Confirm pH remains between pH 3.4 and pH 3.6.
13. Collect precipitate by centrifugation in nitrogen atmosphere.
14. Wash isolated precipitate on the centrifuge first with 5% aq. ascorbic acid (173.15 kg) followed by absolute ethanol (115 kg). For every kilogram of copper (I) chloride used in the pure chelation process, the 5% ascorbic acid solution will require 7.36 kg water and 0.37 kg ascorbic acid. For every kilogram of copper (I) chloride used in the pure chelation process, use 5.32 kg 200 proof ethanol.
15. Vacuum dry precipitate at 60° C. 65° C. for at least 24 hours. Use at least a 26" vacuum.
16. Mill the precipitate through 0.25 in. round-holed screen and hammer forward on high speed.

Comparison of Yield

Using the pure chelation process to chelate copper with nicotinic acid, the theoretical yield of using 22 kg of copper (I) chloride is 76.72. The process above resulted in 74.50 kg copper nicotinic acid. Thus the yield was 97.11%. The conventional process produced 1.086 kg copper nicotinate when the theoretical yield is 1.422 kg, thus the yield was 76.37%. Therefore, the pure chelation process resulted in a greater yield of copper nicotinic acid than the conventional method.

Comparison of Oxidative Quality

Equal amounts of chelated copper made from the conventional method and the pure chelation process were mixed with water. The time for copper nicotinate, the product of the conventional method, to change to the oxidized blue color was around a minute. The time for copper nicotinic acid, the product of the pure chelation method, to change to the oxidized blue color was a few minutes. Thus the copper nicotinic acid produced from the pure chelation process has a delayed oxidation compared to the copper nicotinic acid produced from the conventional method.

Figure 3:
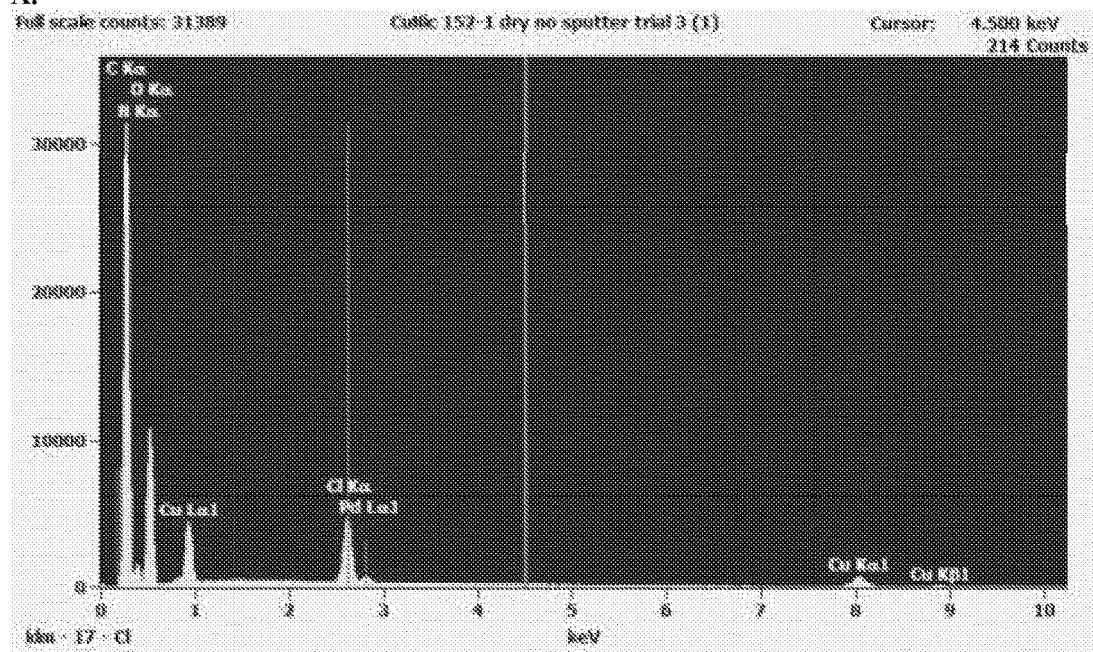
FIG. 3 depicts the energy dispersive spectroscopy (EDS) results of dry copper nicotinate, the copper chelate produced using the conventional method. Panel A depicts the EDS spectra while panel B depicts quantification of the spectra in panel A.
Figure 4:
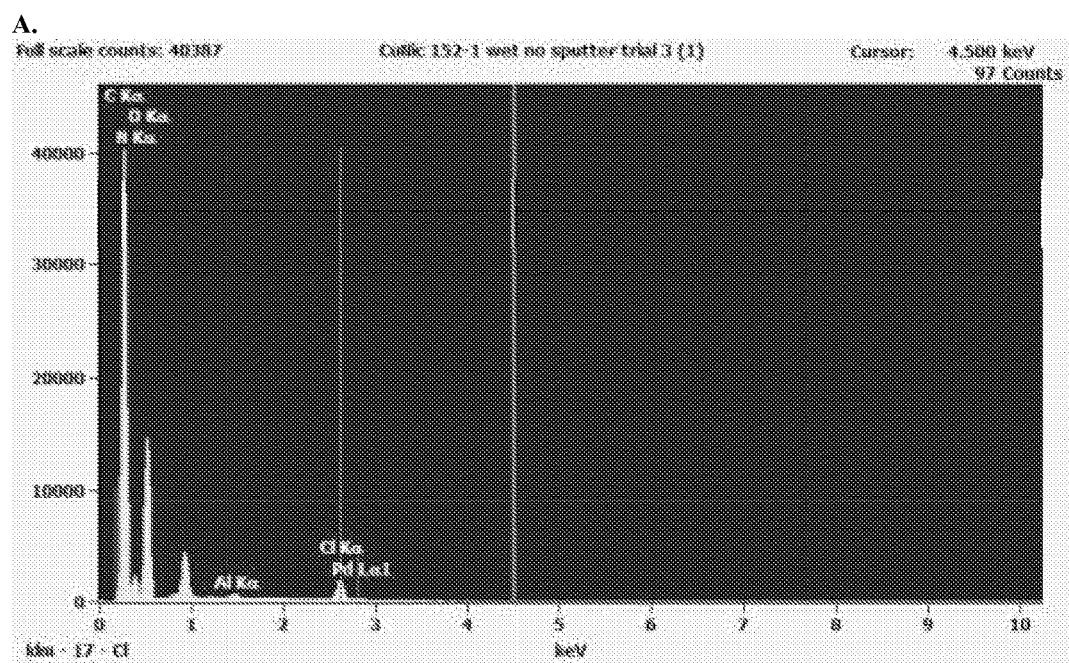
FIG. 4 depicts the EDS results of wet copper nicotinate, the copper chelate produced using the conventional method. Panel A depicts the EDS spectra while panel B depicts quantification of the spectra in panel A.
Figure 5:
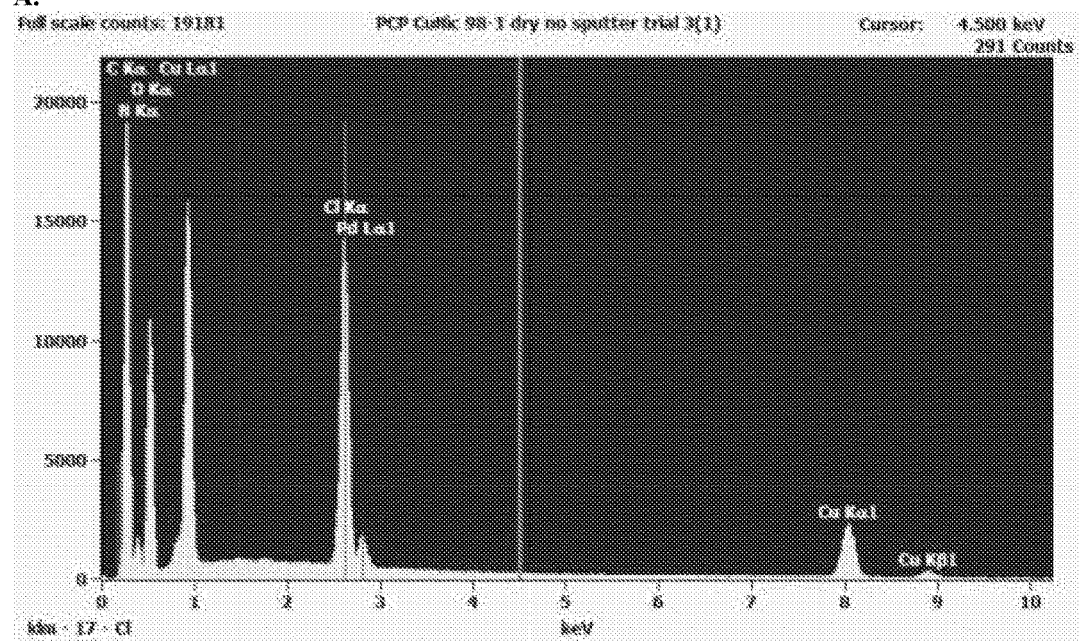
FIG. 5 depicts the EDS results of dry copper nicotinic acid, the copper chelate produced in using the pure chelation method. Panel A depicts the EDS spectra while panel B depicts quantification of the spectra in panel A.
Figure 6:
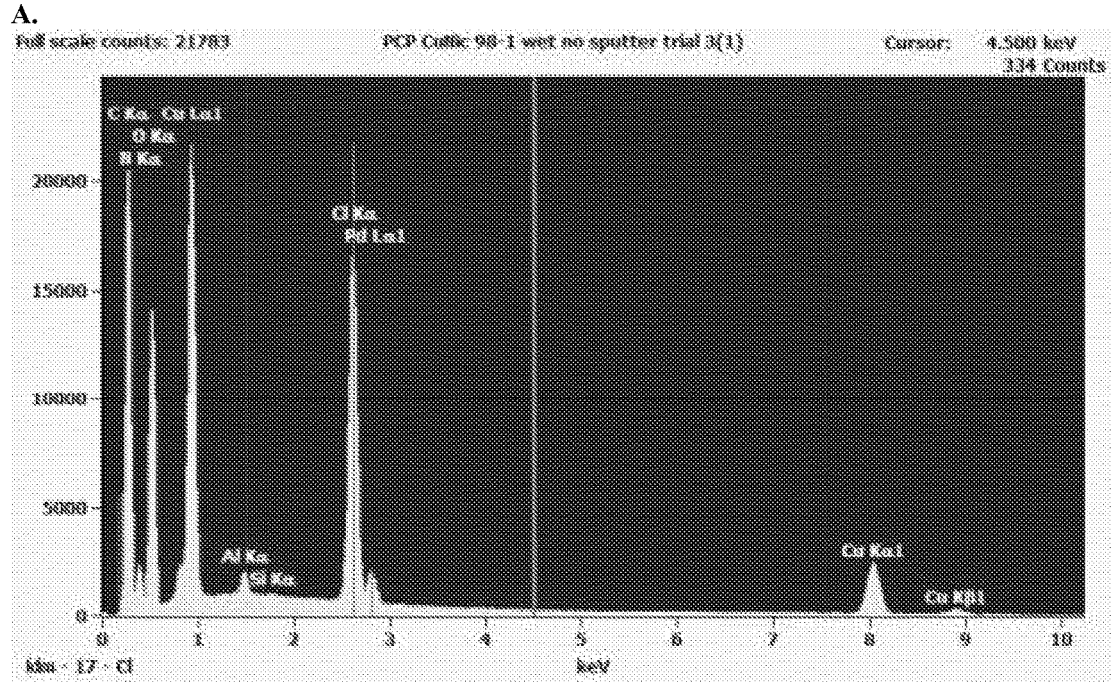
FIG. 6 depicts the EDS results of wet copper nicotinic acid, the copper chelate produced in using the pure chelation method. Panel A depicts the EDS spectra while panel B depicts quantification of the spectra in panel A.
Figure 7:
FIG. 7 depicts the scanning electron microscope image of a copper chelate produced using the conventional method (A) and of a copper chelate produced using the pure chelation process (B).
Figure 7:
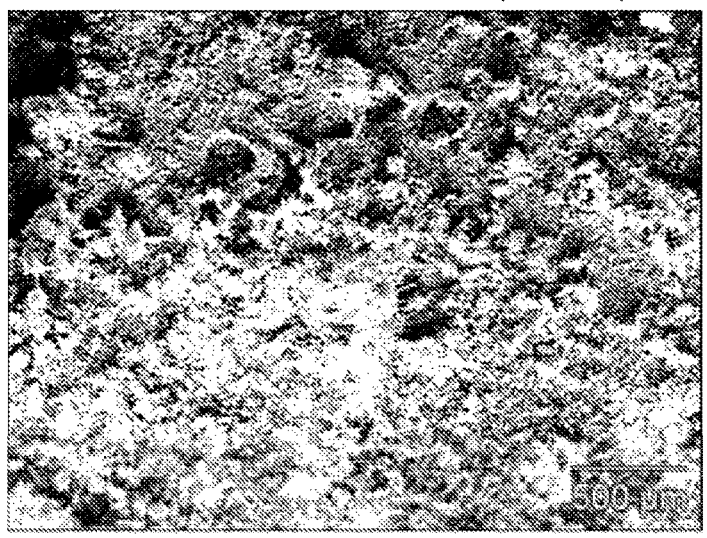

Energy dispersive spectroscopy analysis of the chelated copper furthered showed different reactions to oxidation between the copper nicotinate and the copper nicotinic acid. In dry powder form, copper was 9.82% of the copper nicotinate. FIG. 3B. After the copper nicotinate sample is wetted, the spectra lost the K$\alpha$1 and K$\beta$1 copper peaks. FIGS. 3A and 4A. The distribution of copper, chloride, carbon, hydrogen, oxygen, and nitrogen in copper nicotinate also changed; copper was not detectable in the composition. In the dry powder form, copper was 22.90% of the copper nicotinic acid. FIG. 5B. After the copper nicotinic acid sample is wet, the spectra did not change significantly nor did the distribution of copper, chloride, carbon, hydrogen, oxygen, and nitrogen. FIGS. 5A, 5B, 6A, and 6B. The amount of copper in the wet copper nicotinic acid was 21.7%. FIG. 6B.

Comparison of Transdermal Bioavailability

When the dry powders of copper (I) nicotinic acid made from the conventional method and the Pure Chelation Process were rubbed on the surface of skin, only the dry powders the copper (I) complex made from the Pure Chelation Process disappeared from the surface of the skin. However, neither wetted powders of copper (I) nicotinic acid made from the conventional method nor from the Pure Chelation Process could be rubbed into skin.

What is claimed is:

1. A method of synthesizing copper nicotinic acid, the method comprising the steps of:
    mixing copper (I) chloride in a solution of hydrochloric acid in a first reactor charged with water to produce an aqueous solution of metal ions;
    solubilizing nicotinic acid in a second reactor charged with water in the presence of ascorbic acid to produce an aqueous solution of nicotinic acid;
    heating the aqueous solution of nicotinic acid to a temperature of at least 70° C.;
    mixing the aqueous solution of metal ions with the heated aqueous solution of nicotinic acid gradually to produce an aqueous solution containing a metal chelate, wherein the aqueous solution containing the metal chelate is maintained at a temperature of at least 70° C.;

stirring the aqueous solution containing the metal chelate for at least one hour while maintaining the aqueous solution containing the metal chelate at a temperature of at least 70° C.;

cooling the aqueous solution containing the metal chelate at room temperature; and adjusting the pH of the cooled aqueous solution containing the metal chelate to between about 3 and about 4 to precipitate the metal chelate product, wherein the method is conducted in an oxygen-free environment.

2. The method of claim 1, further comprising the steps of:

collecting the metal chelate product from the cooled aqueous solution containing a metal chelate; and washing the metal chelate product with ascorbic acid followed by absolute alcohol.

3. The method of claim 1, wherein the steps of mixing a metal salt in a solution of hydrochloric acid in a first reactor charged with water is performed in a first nitrogen-purged reactor.

4. The method of claim 1, wherein the metal salt is completely dissolved during the step of mixing the metal salt in a solution of hydrochloric acid in a first reactor charged with water.

5. The method of claim 4, wherein the step of mixing the metal salt in a solution of hydrochloric acid in a first reactor charged with water comprises stirring the aqueous solution of metal ions.

6. The method of claim 1, wherein the step of solubilizing the nicotinic acid in water is performed in a second nitrogen-purged reactor.

7. The method of claim 1, wherein the aqueous solution of nicotinic acid is completely solubilized.

8. The method of claim 1, wherein the temperature of the aqueous solution containing a metal chelate to precipitate the metal chelate product is less than 35° C.

9. The method of claim 1, wherein the temperature of the cooled aqueous solution containing the metal chelate is less than 25° C.

10. The method of claim 1, wherein the step of collecting the metal chelate product from the aqueous solution containing the metal chelate comprises centrifuging the aqueous solution containing the metal chelate in an oxygen-free centrifuge.

11. The method of claim 2, further comprising drying the precipitate in a vacuum at a temperature of between 60° C. and 65° C.

* * * * *